(12) United States Patent
Souryal

(10) Patent No.: US 11,331,111 B2
(45) Date of Patent: May 17, 2022

(54) C-SHAPED ARTHROSCOPIC INTRA-ARTICULAR PIN AIMER

(71) Applicant: Tarek O. Souryal, Dallas, TX (US)

(72) Inventor: Tarek O. Souryal, Dallas, TX (US)

( * ) Notice: Subject to any disclaimer, the term of this patent is extended or adjusted under 35 U.S.C. 154(b) by 251 days.

(21) Appl. No.: 16/804,342

(22) Filed: Feb. 28, 2020

(65) Prior Publication Data

US 2020/0275940 A1 Sep. 3, 2020

Related U.S. Application Data

(60) Provisional application No. 62/811,926, filed on Feb. 28, 2019.

(51) Int. Cl.
*A61F 5/00* (2006.01)
*A61B 17/17* (2006.01)
*A61B 17/32* (2006.01)

(52) U.S. Cl.
CPC .. *A61B 17/1717* (2013.01); *A61B 17/320016* (2013.01); *A61B 2560/04* (2013.01)

(58) Field of Classification Search
CPC combination set(s) only.
See application file for complete search history.

(56) References Cited

U.S. PATENT DOCUMENTS

2021/0186487 A1* 6/2021 Korman ............. A61B 17/1775

* cited by examiner

*Primary Examiner* — Sameh R Boles

(57) ABSTRACT

This disclosure provides an apparatus and method for manufacturing a arthroscopic intra-articular pin aimer is provided. The arthroscopic intra-articular pin aimer is arthroscopic intra-articular pin aimer meant to guide and change direction of arthroscopic, intra-articular pins used to drill within a joint. The arthroscopic intra-articular pin aimer includes a partial loop formed to capture an intra-articular device entered into a joint; an extension neck connected to the partial loop; and a handle connected to the extension neck.

2 Claims, 2 Drawing Sheets

C-SHAPED ARTHROSCOPIC INTRA-ARTICULAR PIN AIMER

CROSS-REFERENCE TO RELATED APPLICATIONS

This application claims priority to U.S. Provisional Patent Application Ser. No. 62/811,926 entitled C-SHAPED ARTHROSCOPIC INTRA-ARTICULAR PIN AIMER and filed on Feb. 28, 2019. The content of the above-identified patent documents is hereby incorporated by reference.

TECHNICAL FIELD

This invention relates in general to surgical devices, more particularly, to an apparatus for assisting in aiming an intra-articular pin.

BACKGROUND

Surgeries are important procedures for maintaining simplicity and reducing clutter in a small area. For implants, manipulating objects in a hole in a joint created can be tedious and difficult. The components used in these procedures need to be easily guided, which could cause a problem multiple passes are required to grab the object or manipulate the object.

SUMMARY

This disclosure provides a C-shaped arthroscopic intra-articular pin aimer and related methods.

In a first embodiment, a C-shaped arthroscopic intra-articular pin aimer is provided. The C-shaped arthroscopic intra-articular pin aimer is configured to guide and change direction of arthroscopic, intra-articular pins used to drill within a joint. The C-shaped arthroscopic intra-articular pin aimer includes a partial loop formed to capture an intra-articular device entered into a joint; an extension neck connected to the partial loop; and a handle connected to the extension neck.

In a second embodiment, a method for manufacturing a C-shaped arthroscopic intra-articular pin aimer configured to guide and change direction of arthroscopic is provided. The method includes forming a partial loop to capture an intra-articular devices entered into a joint; connecting an extension neck to the partial loop; and connecting a handle to the extension neck.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1A:
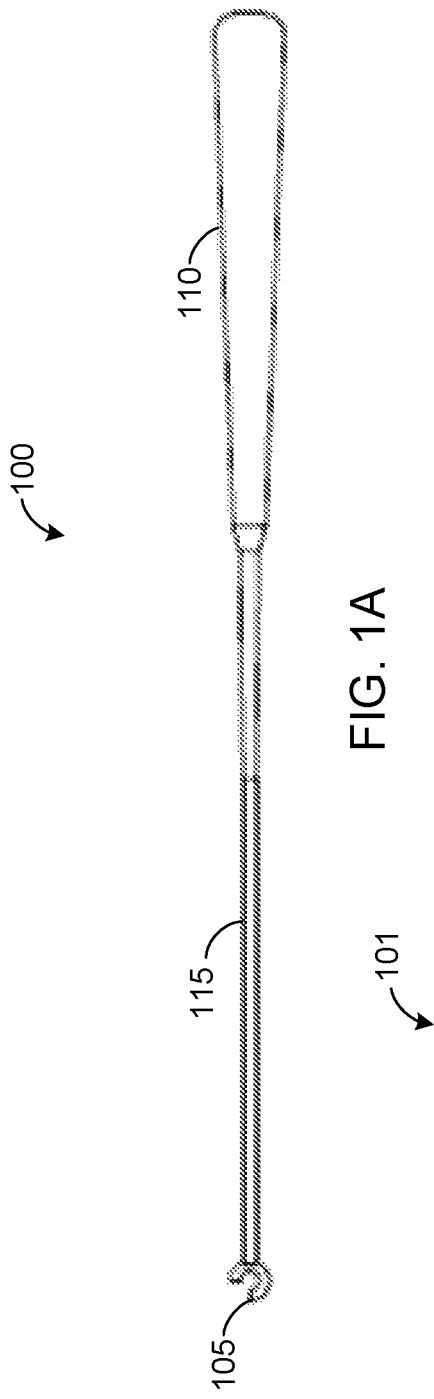
FIGS. 1A, 1B and 1C illustrate an example C-shaped arthroscopic intra-articular pin aimer according to this disclosure.
Figure 1B:
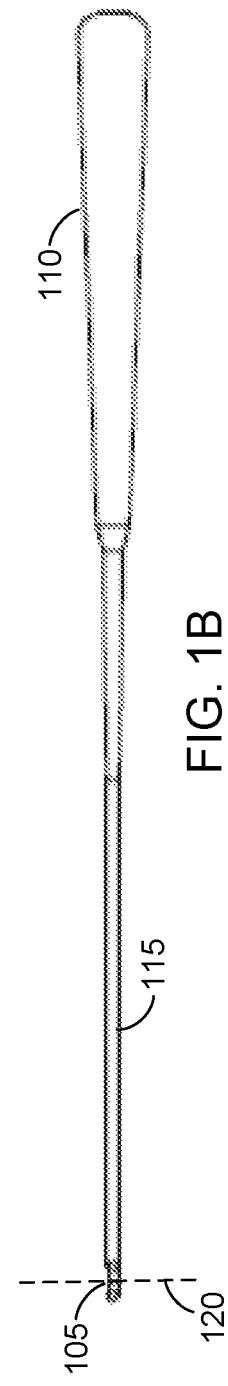
Figure 1C:
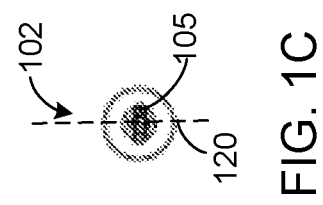
Figure 2:
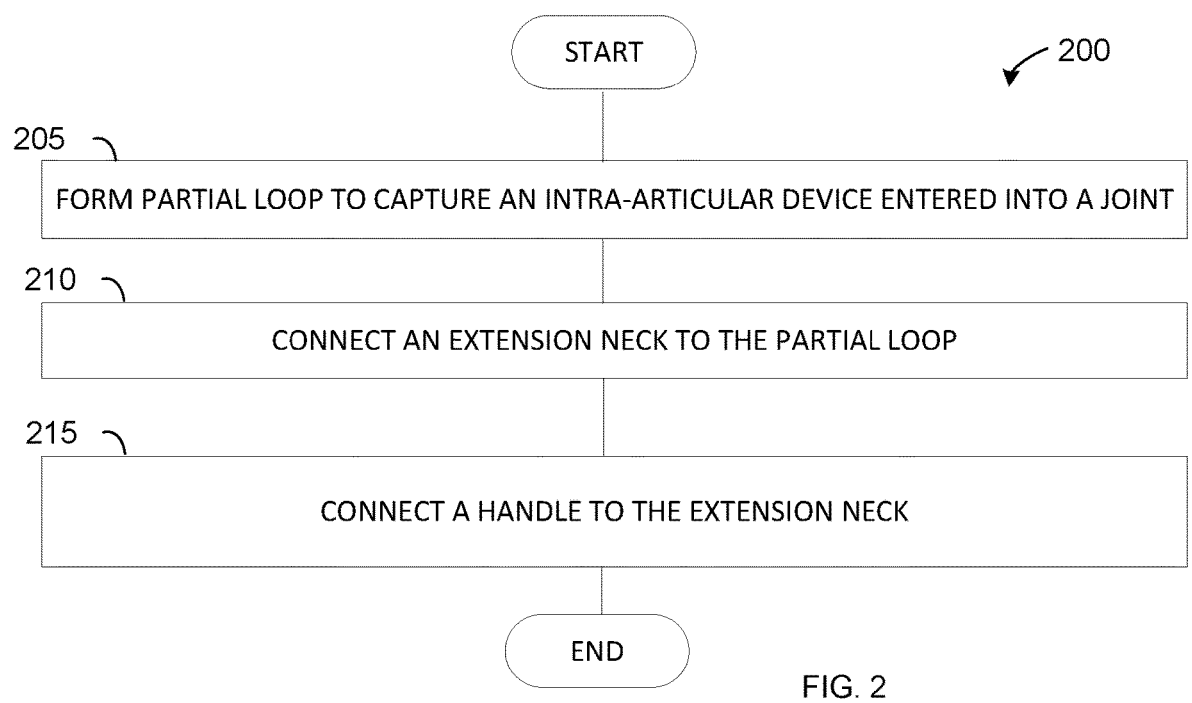
FIG. 2 illustrates an example of creating a C-shaped arthroscopic intra-articular pin aimer 100 according to this disclosure.

FIGS. 1A through 2, discussed below, and the various embodiments used to describe the principles of the present disclosure in this patent document are by way of illustration only and should not be construed in any way to limit the scope of the disclosure.

FIGS. 1A-1C illustrate an example C-shaped arthroscopic intra-articular pin aimer 100 according to this disclosure. FIG. 1A illustrates a C-shaped arthroscopic intra-articular pin aimer 100 according to the various embodiments of the present disclosure. FIG. 1B illustrates a rotated view 101 of the C-shaped arthroscopic intra-articular pin aimer 100. FIG. 1C illustrates a front view 102 of the C-shaped arthroscopic intra-articular pin aimer 100. The embodiments of the C-shaped arthroscopic intra-articular pin aimer 100 illustrated in FIGS. 1A-1C are for illustration only. FIGS. 1A-1C do not limit the scope of this disclosure to any particular implementation of a C-shaped arthroscopic intra-articular pin aimer. While the term "C-shaped" is used for simplicity to describe the partial loop, any similar shape could be used to form the partial loop.

The C-shaped arthroscopic intra-articular pin aimer 100 is a specialized orthopedic device used to guide and change direction of arthroscopic, intra-articular pins used to drill within the joints of humans or animals. The C-shaped arthroscopic intra-articular pin aimer 100 is introduced into the joint using standard arthroscopic portals and, under direct vision or indirect vision, can maneuver a flexible guide pin into optimal positioning for advancement.

The C-shaped arthroscopic intra-articular pin aimer 100 is preferably made of rigid, medical grade metal. The C-shaped arthroscopic intra-articular pin aimer 100 is preferably manufactured to be sterilized for repeated use if necessary. The C-shaped arthroscopic intra-articular pin aimer 100 includes a C-shape partial loop 105, a non-slip handle 110, and an extension neck 115.

The rigid C-shaped partial loop 105 is introduced into a joint such as a knee and is used to capture other intra-articular devices such as drill bits or pins, and with a rotation on the non-slip handle 110, redirect the drill or pin to another location within the joint, then release the drill or pin. The C-shaped arthroscopic intra-articular pin aimer 100 can then be withdrawn from the joint. The C-shaped partial loop 105 is connected to extension neck 115 in a manner that the opening is angled from a centerline of the non-slip handle 110 and the extension neck 115. The loop 105 can represent an arc with a quarter of the material absent from completing a whole circle. The arc can be three quarters of a full circle. While described as a C-shaped partial loop 105, the shape of the instrument could by a deformed C, such as a horseshoe shape, an egg shape with on open end, etc.

The loop 105 can be flat on the top and bottom surfaces on the plane perpendicular to the central axis of the arc. The thickness of the loop 105 in the direction of the central axis of the arc can be less than a diameter or thickness at an end of the extension neck 115 in which the loop 105 is connected. The center of the loop 105 can have a diameter that is approximately the same as a diameter of thickness of the extension neck 115 at the end of the extension neck 115. In certain embodiments, the loop 105 can be a single continuous piece, being not two pieces connected to opposite sides of the extension neck 115.

The C-shaped arthroscopic intra-articular pin aimer 100 has a non-slip handle 110 to grip and redirect intra-articular instrumentation or the C-shaped partial loop 105. The non-slip handle 110 can have a constant diameter or variable diameter. The non-slip handle 110 provides a user the ability to comfortably maneuver the C-shape partial loop 105 during a surgical procedure. The non-slip handle 110 of the component can be enlarged and specially shaped to allow for optimal fingertip control, grip and manipulation of the intra articular component.

The extension neck 115 extends from the C-shaped partial loop 105 to the non-slip handle 110. The extension neck 115 connects to the C-shaped partial loop 105, in one embodiment, approximately at a third of the outside radius from one end of the C shape and approximately two thirds of the outside radius from the other end of the C shape. The connections allow the C-shape partial loop 105 to have a portion for supporting an object grabbed and another portion for aiding in the rotation of the object. The extension neck 115 can be connected to the loop 105 in a manner that the arc of the loop begins on a plane parallel to an end of the extension neck 115 and ends on a plane perpendicular to the extension neck 115.

FIG. 2 illustrates an example of creating a C-shaped arthroscopic intra-articular pin aimer 100 according to this disclosure. For example, the process depicted in FIG. 2 may be performed to manufacture the C-shaped arthroscopic intra-articular pin aimer 100 illustrated in FIGS. 1A-1C.

In operation 205, a partial loop 105 is formed to capture an intra-articular device entered into a joint. The partial loop 105 can manufactured to be rigid or made of a rigid material. A surface of the partial loop 105 in a plane perpendicular to a central axis can be flat or rounded. A thickness of the partial loop 105 in a direction of a central axis of the partial loop 105 is less than a diameter or a thickness of the extension neck 115. A diameter of an inside of the partial loop 105 is greater than a diameter or a thickness of the extension neck 115. The partial loop 105 can be structured in a C-shape, a partial oval, etc. The partial loop 105 can be manufactured in an arc of 270 degrees. The partial loop 105 can be formed from a single continuous piece forming an arc. In certain embodiments, the partial loop 105 can also be formed as separate pieces attached to opposite side of the extension neck 115.

In operation 210, an extension neck 115 is connected to the partial loop 105. An end of the extension neck 115 connects to the partial loop 105 in a manner that the end of the extension neck 115 is perpendicular to a first end of the partial loop 105. An end of the extension neck 115 connects to the partial loop 105 in a manner that the end of the extension neck 115 is parallel to a second end of the partial loop 105. In operation 215, a handle 110 is connected to the extension neck 115.

Although the present disclosure has been described with exemplary embodiments, various changes and modifications may be suggested to one skilled in the art. It is intended that the present disclosure encompass such changes and modifications as fall within the scope of the appended claims.

What is claimed is:

1. An arthroscopic intra-articular pin aimer for to guide and change direction of arthroscopic, intra-articular pins used to drill within a joint, the arthroscopic intra-articular pin aimer comprising:
   a partial loop formed to capture an intra-articular device entered into a joint, wherein the partial loop is rigid and structured in a C-shape;
   an extension neck connected to the partial loop; and
   a handle connected to the extension neck,
   wherein the partial loop includes:
      a first end surface in a plane perpendicular to a central axis of the extension neck, wherein the first end surface is flat, and
      a second end surface in a plane perpendicular to the first end surface,
   wherein a diameter of the partial loop is less than a diameter or thickness of the extension neck,
   wherein a diameter of an inside surface of the partial loop is greater than a diameter or thickness of the extension neck, and
   wherein the partial loop forms an arc of 270 degrees between the first end surface and the second end surface.

2. A method for manufacturing an arthroscopic intra-articular pin aimer meant to guide and change direction of arthroscopic, intra-articular pins used to drill within a joint, the method comprising:
   forming a partial loop to capture an intra-articular devices entered into a joint, wherein the partial loop is rigid and structured in a C-shape;
   connecting an extension neck to the partial loop; and
   connecting a handle to the extension neck,
   wherein the partial loop includes:
      a first end surface in a plane perpendicular to a central axis of the extension neck, wherein the first end surface is flat, and
      a second end surface in a plane perpendicular to the first end surface,
   wherein a diameter of the partial loop is less than a diameter or thickness of the extension neck,
   wherein a diameter of an inside surface of the partial loop is greater than a diameter or thickness of the extension neck, and
   wherein the partial loop forms an arc of 270 degrees between the first end surface and the second end surface.

* * * * *